United States Patent [19]

Gazzani

[11] Patent Number: 4,885,169

[45] Date of Patent: Dec. 5, 1989

[54] COSMETIC COMPOSITION CONTAINING GLYCOPROTEINS FOR THE SKIN CARE

[75] Inventor: Giovanni Gazzani, Como, Italy

[73] Assignee: Crinos Industria Farmacobiologica Spa., Como, Italy

[21] Appl. No.: 688,738

[22] Filed: Jan. 4, 1985

[30] Foreign Application Priority Data

Jan. 9, 1984 [IT] Italy ............................. 19076 A/84

[51] Int. Cl.$^4$ ............................................. A61K 35/38
[52] U.S. Cl. ..................................... 424/104; 424/95; 514/8; 514/844; 514/846
[58] Field of Search ........................... 514/8, 844, 846; 424/95, 104, 105; 530/395, 836, 844

[56] References Cited

U.S. PATENT DOCUMENTS 3,607,650  9/1971  Bertellini et al. ................... 530/395
4,108,849  8/1978  Thomas ............................... 424/95 X
4,425,329  1/1984  Tsutsumi et al. ................. 514/844 X

FOREIGN PATENT DOCUMENTS 1813154  7/1970  Fed. Rep. of Germany ........ 424/95
2036453  12/1970  France .
1166939  10/1969  United Kingdom .
1210022  10/1970  United Kingdom .

OTHER PUBLICATIONS

Horowitz et al., (Eds), The Glycoproteins, vol. 1, Academic Press, N.Y., 1977, pp. 16–17.

*Primary Examiner*—Esther M. Kepplinger
*Attorney, Agent, or Firm*—McAulay Fisher Nissen & Goldberg

[57] ABSTRACT

A cosmetic composition is disclosed containing natural glycoproteins useful with advantageous effect for the skin care.

7 Claims, No Drawings

COSMETIC COMPOSITION CONTAINING GLYCOPROTEINS FOR THE SKIN CARE

FIELD OF THE INVENTION

The present invention relates to a cosmetic composition containing glycoproteins, particularly suitable for skin treatment.

The glycoproteins are known as a class of compounds having highly different and heterogenous function in organisms.

They are widely distributed in the cells of the vertebrates, of the invertebrates, of the plants and of the microorganisms.

In the case of the vertebrates, and particularly in human beings, one of the most important roles fulfilled by glycoproteins which essentially form the mucus, is protecting the internal tissues (in the digesting and respiratory tracts) against mechanical, chemical and microbial damages.

In turn the skin, which under several aspect is like the mucose, is on the contrary efficaciously protected by an inert corneal layer against irritants.

However such a natural protection of the skin is often insufficient mainly when these negative actions are intense and often repeated. In that case the skin appears dry, asphyxiated, starved and senescent, besides being tendentially wrinkled. The present studies on the activities of the natural glycoproteins were and are mainly aimed at the behaviour of the mucosa protected by the mucus in the presence of irritating agents (such as for instance cigarette smoke in the respiratory tract or irritating substances in the digesting tract), and particularly at the reaction of the epithelium to the irritating stimuli.

STATEMENT OF PRIOR DISCLOSURES

FR-A-2300572 discloses a method for the extraction of soluble glycoproteins and/or of mucopolysaccharides and of accompanying substances from the natural sources (animal organs, vegetal tissues and microorganisms) in which they are present. The resulting raw mixtures, either alone or in admixture, can be used in the pharmaceutical, cosmetic or food industry.

More particularly a mixture is disclosed comprising both the subject extracted substances and a mixture of complex lipids, having trophic and protective effects for the skin.

FR-A-2036453 relates to a cosmetic product in which acidic mucopolysaccharides (also indicated as glycosaminoglucuronanes) are present in a percentage of 0.01 to 2% by weight, the cosmetic product being used as soap, shampoo, beauty cream and tooth paste.

GB-A-1166939 relates to the extraction of glycopeptides for which the use as a drug for the treatment of inflammatory diseases and particularly of ulcers is indicated.

OBJECTS AND SUMMARY OF THE INVENTION

It has been now surprisingly found and is the basic principle of the present invention, that glycoproteins of natural origin, as obtained from the mucosa and from the internal epithelial tissues of mammalian beings, in combination with a hygroscopic agent, show with respect to the skin protecting, revitalizing and antiwrinkle activities.

More specifically it has been found that the glycoproteins of natural origin, as obtained by extraction from gastric and intestinal mucosa of mammalians, and the mucines obtained from the mucus as produced by the aforesaid mucosa, show a surprising hydrating, elasticizing and wrinkle activity in the treatment of the senescen forms of the skin, particularly of the skin of the face and of the hands, which more frequently are subjected to physical and chemical attacks. More particularly in the case of the face wrinkles the application of the above indicated glycoproteins shows a favourable influence.

The skin already after the first treatment, is more hydrated, more turgid, more elastic, and more vital and the wrinkles are attenuated and extended.

The beneficial results of the treatment are even more evident in the case of dry, asphyxiated, starved and senescent skin, which is more readily subjected to wrinkles.

It is to be pointed out that, in order for the glycoproteins to show their effect on the skin, it is necessary that the excipients be such that the glycoproteins remain on the skin in solution as much long as possible.

A simple water solution of the glycoproteins has no anti-wrinkle evident action as in the case in which they are carried by means of hygrostatic excipients, by which they are maintained on the skin for a longer time in solution.

Consequently it is the object of the present invention to provide a cosmetic composition for treaating the skin which contains, as the active ingredient, at least a glycoprotein of natural origin or their mixtures, obtained by extraction from gastric or intestinal mucosa of mammalians or from the mucus secreted therefrom, preferably as a water solution, in combination with an hygrostatic excipient.

Among the glycoproteins useful for the cosmetic compositions according to the present invention of particular efficacy is that obtained by extraction from the gastric or duodenal mucosa of swine according to the process disclosed in United Kingdom Pat. No. 1,166,939. This material can be extracted as described in the United Kingdom Pat. No. 1,166,939 from the gastric mucosa or duodenum of mammals or the mucus secreted therefrom by: (a) hydrolyzing these in water at a temperature of about 50° C. to 100° C. for from 10 to 45 minutes at a pH of 1 to 10; (b) removing the acidic products of the hydrolysis; and (c) diluting the product of the previous step (b) with a non-solvent for the resulting glycopeptide to precipitate the glycoprotein or mixture thereof. Preferred non-solvents include acetone or a lower alkanol having one to four carbons.

This glycoprotein, as obtained, is an amorphous, ivory coloured, hygroscopic, water soluble and insoluble in the organic solvents powder, and as regards the composition it may be defined as follows:

|  | Limits: |
| --- | --- |
| Total aminoacids: | 18–28% |
| Hexosamines: | 27–43% |
| Total hexoses: | 25–30% |
| Sialic acids: | 4–5% |
| Viscosity at 20° C. in 0.5 Na Cl | 1.8–2.3 cP |

According to the above definition, the activity of the glycoproteins of the present invention is essentially shown only if in the composition is in a hygrostatic excipient which is capable of retaining for an extended time the active component, namely the glycoprotein, or better its water solution into contact with the skin. Among these hygrostatic sustances, there are to be particularly mentioned glycerine, propylene glycol, sorbitol, generally polyalcohols and the normal hydrating agents such as: NMF (Natural Moisturing Factor), urea, aminoacids, pyrrolidon carboxylic acid, etc.

The normal dosages of use of the glycoproteins of the invention are of between 0.5% and 5% by weight of the composition and the glycoproteins may be combined with vitaminic nutrient factors and aminoacids, placenta extracts, vegetal derivatives etc. A remarkable feature of the present invention is that only the above defined glycoproteins show the aforesaid activity.

In fact, other glycoproteins of natural origin, such as those of milk, do not show the above indicated effect.

This fact has been confirmed by comparative tests, as hereinafter reported, which, also confirm the properties of the glycoproteins according to the present invention.

The tests have been carried out on a total of 20 persons, divided in four groups each comprising five persons.

Groups number one has been treated with placebo, consisting of a 2.5 water solution of glycerine, group No. 2 has been treated with glycoprotein obtained according to the aforesaid U.K. Patent and previously defined, group No. 3 with glycoprotein obtained from milk and group No. 4 with mucine, (the three glycoproteins having been dissolved in glycerine at the concentration of 1%).

The daily treatments were carried out for 15 days consecutively and at the end the results were observed.

The resuming results are reported in the following table:

| Group | Hydrating activity | Elasticizing activity | Anti-wrinkle activity |
| --- | --- | --- | --- |
| 1 | + | − | |
| 2 | ++ | + | +++ |
| 3 | + | + | + |
| 4 | ++ | +− | ++ |

As it is seen from the above table, in the case of group 2 treated with the preferred glycoprotein according to the invention, an optimum activity is observed for all 3 parameters.

A good activity is also detected with the mucine whereas, the activity of the milk glycoprotein is practically absent.

In the following example some cosmetic compositions according to the invention are reported only for illustrating purposes, wherein by "glycoprotein" the substance as above defined and obtained with the process with U.K. Pat. No. 1,166,939 is meant.

EXAMPLE 1

| Creams | |
| --- | --- |
| Glycoprotein | 2 g |
| Glycerine | 10 g |
| NMF | 2.5 g |
| Polyoxyethylenesorbitan monostearate | 4 g |
| Sorbitan monostearate | 2.5 g |
| Spermaceti | 7 g |
| Decyl oleate | 8 g |
| Preserving agent | enough |
| Perfume | enough |
| Water to 100 g | |

EXAMPLE 2

| Fluid emulsion | |
| --- | --- |
| Glycoprotein | 2 g |
| 70% Sorbitol | 13 g |
| Urea | 1 g |
| Stearo-isostearate of glycerol and propyleneglycol | 3.5 g |
| Oxyethylenated fatty alcohols | 2.5 g |
| Cetylstearilic alcohol | 9 g |
| Octyldodecanol | enough |
| Preserving agents | enough |
| Perfume | enough |
| Water to 100 g | |

EXAMPLE 3

| Gel | |
| --- | --- |
| Glycoprotein | 1.5 g |
| Neutralized carboxyvinylpolymer | 1.2 g |
| Propyleneglycol | 8 g |
| Preserving agents | enough |
| Perfume | enough |
| Water to 100 g | |

EXAMPLE 4

| Lotion | |
| --- | --- |
| Glycoprotein | 1 g |
| Glycerine | 7 g |
| 95% Alcohol | 10 ml |
| Preserving agents | enough |
| Perfume | enough |
| Water to 100 mg | |

I claim:

1. A cosmetic composition for hydrating the skin, comprising at least one naturally derived, purified glycoprotein substantially free of low molecular weight products and having been isolated from the gastric mucosa or duodenum of mammals by:
   (a) hydrolyzing said mucosa or duodenum in water at a temperature of 50° C. to 100° C. for 10 minutes to 45 minutes at a pH of 1 to 10;
   (b) removing acidic products of the hydrolysis; and
   (c) diluting the product of step (b) with a non-solvent for the glycoprotein to precipitate said glycoprotein, said composition containing also water and at least one hygrostatic excipient, said composition being characterized by its ability to remain on the skin for an extended period of time.

2. The composition of claim 1, wherein said glycoprotein is extracted from mucus secreted by swines.

3. The composition of claim 1, containing a mixture of glycoproteins.

4. The cosmetic composition according to claim 1, containing at least one supplementary ingredient selected from the group consisting of vitaminic and aminoacids, placenta extracts and mixtures thereof.

5. The cosmetic composition according to claim 1, wherein said hygrostatic excipient is selected from the group consisting of glycerine, propylene glycol, sorbitol, polyalcohols, NMF (Natural Hydrating Factor), urea, aminoacids, pyrrolidone-carboxylic acid and mixtures thereof.

6. The cosmetic composition according to claim 1, wherein said glycoprotein is contained in dosage units varying from 0.5 to 5% by weight of the total composition.

7. The composition of claim 1, also containing cosmetically acceptable ingredients adapted to form a cream, an emulsion or a gel.

* * * * *